United States Patent [19]

Nilsson

[11] Patent Number: 4,812,402

[45] Date of Patent: Mar. 14, 1989

[54] METHOD OF DETERMINING HYPERSENSITIVITY TO AN ALLERGEN

[75] Inventor: Tomas Nilsson, Borås, Sweden

[73] Assignee: Bio-Instructa Labkonsult, Sweden

[21] Appl. No.: 159,514

[22] Filed: Feb. 19, 1988

Related U.S. Application Data

[63] Continuation of Ser. No. 683,399, Dec. 17, 1984, abandoned.

[51] Int. Cl.⁴ .................................................. C12Q 1/04
[52] U.S. Cl. ...................................... 435/29; 435/39; 435/40; 436/501; 436/517; 436/519; 436/513
[58] Field of Search ............... 424/88, 91, 95; 435/29, 435/39, 40; 436/501, 519, 513, 517

[56] References Cited

FOREIGN PATENT DOCUMENTS 2467401  4/1981  France ................................ 436/513

OTHER PUBLICATIONS

Tharp, J of Immunology, 130(4), pp. 1896–1901, (1983).
Wettermark-I, J of Colloid and Interface Science, 73(1), pp. 287–289, (1980).
Wettermark-II, Derwent Abstract 59867, D/33, (1981).
Nakagawa, Allergy 36, pp. 39–47, 1981.
van Toorenenbergen, J. Immunological Methods, 49, pp. 209–213, (1982).
Benveniste, Clinical Allergy II, pp. 1–11, 1981.
Leynadier, Allergy 36, pp. 239–244, 1981.

Primary Examiner—Robert J. Warden
Assistant Examiner—Robert Benson

[57] ABSTRACT

A method is described for the in vitro determination of hypersensitivity to an allergen. The method consists of adding the allergen to a sample containing basophilic leucocytes from the blood of a patient, and then measuring the amount of degranulation of the leucocytes. The allergen is added slowly and continuously, such that the threshold concentration needed to cause degranulation of sensitized leucocytes is reached sometime during the addition step and is present for a long enough period of time to allow degranulation to occur.

9 Claims, No Drawings

METHOD OF DETERMINING HYPERSENSITIVITY TO AN ALLERGEN

This application is a continuation of application Ser. No. 683,399, filed Dec. 17, 1984, now abandoned.

TECHNICAL FIELD

The present invention relates to a method and a device for analysis of the activity of receptors in a sample containing certain cells, e.g. blood cells, where the desired reaction occurs at a certain individually varying optimal ratio between the concentrations of the receptor and the agent with which the receptor interacts.

Within cell biology knowledge has now been acquired of a multitude of reactions, initiated by receptors on cell surfaces. A number of these receptors react according to an all or nothing principle, that is when optimal conditions prevail between the receptor and the agent, which effects it, a "total reaction" occurs which cannot be immediately repeated again by the same cell. Often a certain concentration of agent in relation to the concentration of receptors has to be attained in order that the reaction shall take place. When this threshold is exceeded the reaction takes place rapidly and completely. Other receptors have, apart from a minimum threshold, also a maximum threshold for the amount of agent which can release the reaction. This concerns e.g. the reactions of mast cells and basophilic leucocytes in allergic individuals, when adequate allergen is exposed to the cells.

Another circumstance common to such cell reactions is that large individual variation exist concerning the reaction ability of the receptor, which concentration ratio is optimal and also how the released reaction then manifests itself in the form of other reactions in the tissue.

BACKGROUND OF THE INVENTION

Testing for allergy ultimately constitutes an analysis of the activity of receptors of basophilic leucocytes and is thus referred to the area of application of the invention. In such testing, in most places, a practical working schedule with approximately the following appearance is used:

The patient has acquired a picture of his symptoms, which constitutes the base of the case history, which is noted by the physician. On the basis of his own experiences, the patient is often able to specify the allergen (e.g. grass or cat) and with special knowledge founded on knowledge of probable allergens in various environments, seasons etc the physician can obtain a fairly good picture of which allergens are of interest.

In order to objectify this there are existing tests.

These are of two types, one tests on the patient himself (in vivo tests), another tests on tissue samples, usually blood samples from the patient (in vitro tests). These are in brief as follows:

In vivo the reaction in question may be elicited by imitating the process which gives the symptom. Thus, the reaction may be provoked by the patient inhaling the allergen, whereby hay-fever and asthma attacks may be started. The allergen may be instilled into the eyes and cause running eyes etc.

The most common in vivo test is, however, skin prick tests, of which the most common is so-called prick test, where a drop of the allergen in solution or in powder form is applied to the skin whereupon a slender lancet is pricked through the allergen and underlying skin. After 20–30 minutes the result is read, which constitutes an itching blush of which the diameter is a rough measure of the degree of allergy. In a particular drop there is usually also added a reference substance allowing better judgement of the reaction (histamine).

The test is usually performed on the forearm, this to allow isolating of the reaction from the rest of the body if any vigourous reaction results. It is then easier to treat a possible generalization of the reaction (anaphylactic shock), which can be fatal.

In this way the so-called type 1 reaction (hay-fever, certain forms of asthma and rashes, red eyes and hypersensitivity towards certain drugs, etc) may be objectified.

In these tests, the allergen is allowed to diffuse into those cells which have receptors on the surface directed towards the allergen. These cells are the so-called mast cells in the tissues. Their counterpart is the blood vessel in the so-called basophilic leucocytes, which are present in a low number in comparison to other blood cells (around 0.5% of all leucocytes or white blood cells).

When the mast cell or the basophilic cell meets with an allergen under certain conditions, it empties its content of small granules, granula, from which then histamine is liberated and causes the symptoms as it reacts with histamine receptors on other cells.

A number of tests may also be executed in vitro in order to objectify or confirm an allergy.

The most common method in Sweden is PRIST ®- test (Paper Radio Immune Sorbent Test, Pharmacia), wherein the concentration of IgE-molecules is measured. It is usually higher in allergic persons than in healthy persons. IgE are those molecules which constitute a part of the receptor, on the mast cells and basophilic leucocytes, for the allergen. IgE is formed by lymphocytes and particularly when these are stimulated by an allergen. Lymphocytes release allergens in the body fluids and a small portion of these get caught on the mast cells and basophilic leucocytes (also other cells in certain cases). Less than 0,1% of IgE is bound to the reacting basophilic leucocytes, but there is probably a very large variation in this among different individuals.

A positive PRIST does thus not mean that an allergic reaction is measured but that the fact is made use of that many, but not all, allergic persons have a higher concentration of IgE in the blood than healthy people. It is also possible to measure the concentration of specific IgE for a large number of allergens. The test is then called RAST © (Pharmacia). Often there is a good correlation between RAST and a performed skin prick test, at least if the same allergen is used as the reagent of those tests.

These two tests are used to a varying extent to complete the case history and skin prick testing.

Relatively little blood is consumed for the Rast test, which utilizes radio logical technique, which is common technique of analysis in larger hospitals in Sweden. The cost for a test, however, is so high that most often only in vivo-test are carried out.

There are also other methods for in vitro tests for allergy. For research purposes the liberation of histamine or other substances from mast cells and basophilic leucocytes upon contact with allergens are used, but this methodology is complicated and expensive, with results which are often difficult to evaluate, since the proportion of histamine in the blood of healthy people can not yet be reliably determined and there are large difficulties in directly measuring in a blood sample, possible changes. In practically all described methods it has been necessary to first enrich and wash the cells before reaction, which then has to correlate with with the total histamine content of the cells. This requires large volumes of blood per allergen tested.

Especially in France, techniques have also been used where the basophilic leucocytes have been investigated in connection with allergy. In brief, the methodology has been approximately of the following type, which also applies if measurements on liberation of histamine have been made. A blood sample is divided into portions, possibly after a less complicated enrichment step. To each portion a specific proportion of allergen is added. Usually six portions containing some ml basophilic suspension are used to which a series of concentrations of allergen (to the extent as the reactive part of the allergen extract can be measured) from about 1 ng/ml in steps of a power of 10 to up to 1 mg/ml have been added. This varies to some extent with the allergen preparation, but a spectrum of 1 million concentration units was necessary to be included due to individual variations. After a waiting period of about half an hour the basophilic leucocytes were then counted in dried and stained blood smears in a microscope.

Due to the large amount of work, this has not had widespread use as a method for allergy tests, despite that the actual reaction of the effector cell in allergy disorder is measured on a sample of blood delivered to a hospital laboratory instead of being measured on the patient as in the skinprick-test.

Very recently, a couple of publications have described the use of high capacity cell counters in the evaluation of the reaction, but still the blood volume is large if many allergens are tested, since several portions are used for each allergen tested.

TECHNICAL PROBLEM

The present known applicable methods for analysis of the activity of receptors of certain cells, have thus lead to extensive, time consuming procedures. In particular, this has implied a serious problem in allergy tests where generally testing of a number of allergens, are required in the order of 10–20, for each patient, which thereby, as it appears from the preceeding, in their turn have been divided into several different samples. For several patients a large number of samples were thus needed, which meant complicated handling and required a large amount of blood.

THE SOLUTION

By the present invention a method is provided which permits clinical application of reactions of the type mentioned in the beginning under the heading "Technical field", e.g. for allergy diagnostics, whereby the required number of sample, the blood volume, and the amount of work for the execution of the analysis, is minimized and the method may also be adapted for automation.

This has been achieved in that the cells in one and the same sample are exposed to an increasing concentration of agent under stepwise or continuous addition of agent, where this occurs in an extended lapse of time, up to a certain predetermined concentration, so that the cells are exposed to a concentration of agent, which is optimal for attaining an adequate reaction, during such a long time that the intended reaction is allowed to take place. If the final concentration of agent then exceeds the optimal it is unimportant since cells already have reacted. The sample is ultimately analysed, after the addition process, with respect to the result of the reaction.

ADVANTAGES

Through the invention the advantage is obtained that only one sample is required for analysis of the reaction of the cells towards an agent. Despite this, an adequate expression for the optimal reaction of the cells is obtained without being necessary to adapt the addition of the agent to the optimal concentration.

This is a great advantage, in particular in allergy testing where in general a large number of agents are tested, whereby a plurality of samples for each agent produces a large total number of samples, which thus is reduced considerably through the invention.

Additional advantages are obtained when the basophilic leucocytes in blood samples can be utilized in allergy diagnostics. The advantages are:

Principally, the same initial effector mechanism is studied as the one which releases the symptom of the patient.

Blood sample may be sent to a laboratory instead of the patient taking off work to occupy a hospital waiting room, like in skin prick test.

The risk of anaphylactic shock or other reactions during the testing disappear. Certain drugs and other potentially dangerous allergens may be tested without injury to the patient.

Only the real allergic reaction is studied, other unspecified reactions of other types are eliminated and the diagnosis becomes more reliable.

THEORETICAL BACKGROUND

The mechanism of the reaction between basophilic leucocytes and allergens may be described as follows.

On the cell surface there are receptors for IgE-molecules, which are produced by lymphocytes and released to the body fluids, which in all human beings contain a small amount of IgE. In allergic persons the concentration are often strongly increased (compare PRIST ® and RAST ® test).

There is an equilibrium between the number of free IgE-molecules and the number bound to the mast cell and the cell. Each cell has a large number of IgE-receptors (40–500 000 per cell).

IgE reacts with the allergen in such a way that several IgE are bound together. Both free and cellbound IgE bind allergen, but only those bound produce a continued reaction.

The proportion of receptors per cell, the relative number of IgE-molecules bound, the ratio between free and bound, the affinity of IgE towards the allergen and the ability for continued reaction vary from individual to individual. This means that the amount of allergen which has to be added to a sample with cells or through the skin in skin prick testing varies considerably with the individual. In addition, the requirement of not too much and not too little allergen have to be satisfied.

The reaction between allergen and IgE has to be effected in the following way in order that the continued reaction shall be released: Each IgE molecule bound to the cell surface bound can react with the allergen but only a small portion of all IgE is needed in order that the reaction may start, maybe in the order of ten. The initiating factor is the change which occurs around the IgE-molecule in the cell membrane when an allergen simultaneously binds together two or possibly more IgE-molecules.

If there are too few allergens in relation to the IgE then two IgE will not be able to simultaneously bind the same allergen whereby nothing further occurs. If there are too many allergen molecules which can bind IgE, each IgE will bind the allergen, but the probability of two simultaneously binding the same allergen is reduced. When the ratio between allergen and IgE is optimal, i.e. two or several IgE are bound together by allergen then the following occurs:

Calcium ions can leak in through a "hole" in the cell membrane, which is held open for a short time, probably seconds. If enough calcium enters into the cell, mechanisms are released which within a couple of minutes have ejected the granules out of the cell. From these are liberated histamine and other molecules and the allergic reaction has started.

The reaction may be measured in various ways, of which one way is constituted by counting the basophilic leucocytes, where the degranulated cells are not included. There now, exist automatic devices for counting the basophilic leucocytes, i.e. TECHNICON® H6000. For research purposes methods are also used where liberated substances are analyzed as a measure of the reaction. These methods are, however, presently laborious and expensive.

The above described reaction occurs very rapidly and the critical event in this is that cross binding together of at least two IgE per allergen must take place. This binding is a very fast reaction while the liberation of histamine subsequently takes a few minutes. Once the cell has reacted, it is emptied of granules and cannot react further or (as far as it is known at least in human beings) cannot quickly take up granules again. It does not matter then if the concentration of allergen is too high if the reaction already has taken place.

This means that the cells may be exposed to an increasing concentration of allergen in one and the same blood sample, up to a predetermined final concentration under the condition that the time, during which the optimal concentration of allergen for the reaction is surpassed, is sufficient, but not too long since the reaction may possibly be inhibited. Thus optimum interval is passed during a few minutes whereafter the allergen may rise to very high levels without the already produced degranulation being influenced. This resembles the natural process in the body tissues when the allergen diffuses to the receptor.

BEST MODE OF CARRYING OUT THE INVENTION

In brief the invention thus implies that the agent, such as an allergen with which the cell is to react, is added in a slow process. The process shall then proceed for such a long time that the receptors of the cells attain their reaction level and that the concentration does not deviate from a corresponding level during a period of time which is sufficiently long for the intended reaction without it being disturbed by further substantial addition of the agent in question. This delayed process of addition may be carried out in two ways.

1. Stepwise addition to a blood sample with intermediate time interval in increasing concentration of the agent in question. Such a stepwise addition may be carried out manually or in an analysis apparatus by use of pipettes or automatically in a continuous flow system. Both these applications are described in 1a and 1b, respectively, in the following.

1a. By use of pipette:

From the patient 10 ml of blood is taken in a Vacutainertube with added EDTA, which is mixed by rocking the tube. To this volume of blood is added 20-25 $\mu$l Heparin solution (Lövens I.V Heparin 5000 IE/ml, diluted to 500IE per ml with isotonic sodiumchloride).

The tube is rocked until mixing has taken place. In certain cases, up to a week old EDTA-blood may be used if the sample has been stored in a refrigerator, possibly after addition of certain nutritive substrates.

The blood is divided in portions of 300 $\mu$l each in suitable tubes, e.g. polyethylene tubes. 10 ml is enough for about 30 portions and thus principally for 30 allergy tests. To one of the tubes 10 $\mu$l of 0.06M $CaCl_2$ and possibly 0.3M $MgCl_2$-solution is added.

To another tube, this is not added (control tube).

Allergen, e.g. from DOME (skin prick test solution, e.g. 5-grass 4000 PNU/ml in 50% glycerine) is diluted in a number of tubes as follows:

The diluent solution is albumin solution 1.6 g/l (Kabi, albumin 200 mg/ml diluted with isotonic sodium chloride solution, sterile executed.

Solution 6: Extract diluted 1+1 with diluent solution.

Solution 5: The above diluted 1+9 with diluent solution.

Solution 4: The above (5) diluted 1+9 with diluent solution.

Solution 3: The above (4) diluted 1+9 with diluent solution.

Solution 2: The above (3) diluted 1+9 with diluent solution.

Solution 1: The above (2) diluted 1+9 with diluent solution.

Possible further dilution may be necessary with certain commercial allergen preparation. The principle is that the concentration in the sample, when the solution is added, shall be progressively increasing, preferably according to an exponential curve.

The blood samples are placed in water bath at 37° C.

10 $\mu$l of these solutions are subsequently added to the two test tubes in the water bath at an interval of a few minutes between each addition, starting with the most diluted solution. When the most concentrated solution also has reacted for some minutes, the reaction is interrupted with an excess of EDTA solution, e.g. 50 $\mu$l 10% $K_3EDTA$ in water, whereby calcium ions are bound by chelation.

The tubes are subsequently placed in a TECHNICON® H6000 apparatus or other commercial detector useful for measuring the reaction.

A positive test implies that granulated basophilic leucocytes of the patient have been reduced in number, often disappeared completely, as the detector sees them. (In the control tube without calcium ions the number has not been reduced).

1b. By addition of allergen in a flow system:

A continuous-flow equipment is assembled so that a blood sample is sucked into the hose at a certain speed (e.g. 500 $\mu$l/minute) and then passes "stations" with addition of Ca-Mg solution and allergen in progressively increasing (see "Solution 1-6" under 1a) concentration at certain intervals of time. As the sample appears in the other end of the system, an EDTA addition has also been carried out and the sample may be collected in a tube which subsequently is positioned in the detector.

With such an arrangement it is possible to make a direct connection to an automatic detectorsystem, e.g. the basophil channel of a H6000-apparatus.

2. Continuous addition by diffusion, eluation or dissolution of the agent, which may be an allergen, to a blood sample or by chemical reaction with the same. This variation of the invention is described under 2. in the following:

2. On one end of a suitable carrier e.g. a stick or strip of inert plastic material is placed in one end of a device which continuously releases increasingly higher concentrations of allergen or other agents for other receptors which react, on the basis of this principal. Thus by this arrangement is also obtained a progressively increasing concentration.

The liberation in the sample must occur in such a manner that the optimum concentration interval is crossed traversed during sufficient but not too long a time. A stick suitable for the purpose may be produced by e.g. GELBOND ® or drawing film in which the one side is hydrophilic. To this surface agarose can be bound. The agarose can then be used to bind the allergen solution, where the allergen diffuses into the agarose. If additional, possibly more concentrated agarose or gelatine is placed on top of the previous agaros, after this has dried, a concentration gradient can by means of diffusion be set up within a very thin layer of agarose, when everything has dried after the second diffusion. On top of this other substances, e.g. gelatine, can where a lower concentration of allergen has been placed, also get absorbed and dried. If this stick is placed in a tube with blood or a suspension of cells in a suitable liquid from allergic persons, if a suitable concentration of agaros has been used, a degranulation reaction can be reached. To the sample is also added calcium (in rapidly soluble form), whereafter the stick is positioned in the tube during a certain time. Thereafter, it is removed and after eventual addition of EDTA, the sample is ready for the detector. This method resembles the diffusion of allergen to the mast cells in a skin prick test.

Example of production of stick tested for grass, broadleaf tree, daisy, mite, dust, cat, and horse on a number of allergic persons.

DOME skin prick test allergen as above is used, taken directly from the package.

A warm 0.25% agarose solution (SEAKEM) in water is poured out onto a hydrophobic surface which is horizontally positioned to a layer of about 3 mm. After gelling, cylinders are punched out with the same diameter as the width of the GELBOND ® stick and immediately placed adjacent at the one end of the hydrophilic side. On this gel cylinder 3 $\mu$l of current skin prick test solution is placed and this is allowed to diffuse while a heating fan is used to carefully dry the gel or it is positioned in such a way that the gel is hanging upside down over the edge of a table and is hereby dried. When the cylinders have dried up to a spot, a similar cylinder is placed on top of the spot and the evaporation step with simultaneous back diffusion of the allergen is repeated. The stick is ready for use.

Take e.g. 400 $\mu$l of blood with additions as described or cellsuspension. Add calcium solution according to the previously described manual method 20 $\mu$l 0.06M Ca and possibly 0.03M Mg. Place the tube in a water bath at 37° C. Place a stick in the tube and shake intermittently the tube or stir with the stick so that the blood is brought in contact with the whole surface agarose of at least for shorter periods. Remove the stick after about 30 minutes and add EDTA in order to stop the reaction by binding the calcium. The tube is subsequently placed in the detector. The positive reaction is as described above.

The stick indicated in the example has been tested by letting radioactively marked protein, having a molecular weight of 22 000 (most allergen are of this size) diffuse out into the blood as described. After 30 minutes, 90% of the radioactivity was outside the stick, after 5 minutes approximately a third. By modification of binding substance, possible protein binding, of the allergen etc. this can be varied.

Continuous addition by diffusion or eluation may also be carried out from a substance which itself is being diluted in the blood. Simplest is a "tablet" made of e.g. gelatine, which is completely dissolved and disappears as an indication that the solvation reaction is completed.

The allergen may also be bound to an insoluble substance, e.g. a tablet of the slow release type, common in connection with drugs.

The allergen may also be dissolved from the tube itself or from a cork fitting into the tube, which after corking is turned upside down for reaction and then after "de-corking" is placed in the detector.

It is also possible to use a cork, fitting the tube and which is designed as a container. To the cork is attached a paper strip or a capillary containing an absorbing material, e.g. a thread which has been soaked in allergen solution with suitable additives and dried. The tube with blood is corked with this device. The capillary shall reach down to the blood. Eluation solution is then poured into the cork and is absorbed by the thread whereby the allergen successively is liberated in the other end of the capillary into the blood.

The allergen may also be added to the sample chemically bound to e.g. a protein, from which it is successively liberated to the sample by chemical reaction.

In all these cases, the allergen thus forms a body, possibly together with a carrier, from which body it is slowly liberated into the sample by diffusion, eluation, dissolution, or by a chemical reaction. It is desirable that the analysis may be performed in an analysis apparatus, which is of particular value in allergy tests, where each patient in general must be tested for a large number of allergens. How such an analysis apparatus may function, has been described under 1b, where stepwise addition is uded in a continuous-flow system. However, also the now described method of addition continuous addition by liberation into the sample from an allergen body, permits excellent possibilities to automate the analysis. The analysis apparatus is so designed that it to successively added samples, which preferably are collected groupwise for each patient, be added to said body of allergen. Thereafter, the respective sample is left in a resting position so that the allergen is liberated into the blood. After an adequate period of time the samples are then fed into a detector, which may be of the previously mentioned kind, for analysis. By a suitable arrangement, all samples for one and the same patient maybe analyzed in direct succession after each other, which facilitates the reporting and makes it more reliable. Before the analysis, the samples do not have to come in contact with any flow system, but may pass the system as static amounts of sample, which reduces the need for cleaning of the apparatus and eliminates the risk for intermixing of quantities of samples and contamination with unintended allergen.

The method of the invention is naturally not limited to the above described embodiments and to the reaction of basophilic leucocytes with allergen. Other fields of application may be the study of germicidal ability or neutrophilic leucocytes in patients with defective immune defense (e.g. cronic granulating disease, myeloperoxide deficiency and others) and the reaction of trombocytes on stimulus of the type collagen or of the products of the protease cascade systems.

I claim:

1. A method of testing a patient for hypersensitivity to an allergen comprising the steps of
    (a) providing a sample containing basophilic leucocytes from the blood of said patient;
    (b) contacting said sample with said allergen at a concentration level below the degranulation reaction threshold concentration;
    (c) increasing the concentration level of said allergen in said sample by addition of allergen to said sample until the concentration level is above said threshold concentration, said addition being at a rate slow enough, such that said basophilic leucocytes have sufficient time to undergo degranulation;
    (d) measuring the amount of degranulated basophilic leucocytes as a measure of the hypersensitivity of said patient to said allergen.

2. The method according to claim 1, wherein a plurality of samples from said patient are tested and a different allergen is added to each sample in order to test for hypersensitivity to said different allergens.

3. The method according to claim 1, wherein the concentration level is increased by the stepwise or continuous addition of said allergen to said sample.

4. The method according to claim 1, wherein the contacting of said allergen with said sample is by providing said allergen for contacting said sample in a vehicle means whereby said allergen is slowly released from said vehicle into said sample.

5. The method according to claim 4 wherein said vehicle for said allergen is a liquid and the allergen concentration is incrementally increased by the dropwise addition of the liquid vehicle containing said allergen.

6. The method according to claim 4, wherein said vehicle for said allergen is a solid carrier having said allergen distributed therein and incorporated in a manner such that said allergen is released into said sample over an extended period at said slow rate.

7. The process according to claim 6, wherein said solid allergen-containing carrier is affixed to a stick which is to be dipped into and maintained in contact with said sample.

8. The process according to claim 6, wherein said solid allergen-containing carrier is deposited on the plugs provided for closing the blood sample tubes and effecting contact between said allergen-deposited plugs and the samples in said tubes by inverting the tubes.

9. The process according to claim 6, wherein said allergen is incorporated into soluble tablets which are introduced into said sample to effect contact between said allergen and said sample.

* * * * *